United States Patent [19]

Hammond, III et al.

[11] 3,981,175

[45] Sept. 21, 1976

[54] METHOD OF AND APPARATUS FOR NONDESTRUCTIVELY DETERMINING THE COMPOSITION OF AN UNKNOWN MATERIAL SAMPLE

[75] Inventors: Ogden H. Hammond, III; Francis I. Baratta, both of Arlington, Mass.

[73] Assignee: Massachusetts Institute of Technology, Cambridge, Mass.

[22] Filed: May 19, 1975

[21] Appl. No.: 578,446

[52] U.S. Cl. .............................................. 73/15 R
[51] Int. Cl.² ............................................ G01N 25/00
[58] Field of Search .............. 73/15 R, 15 A, 15 B, 73/61.3

[56] References Cited
UNITED STATES PATENTS

| | | | |
|---|---|---|---|
| 2,264,968 | 2/1941 | De Forest | 73/15 |
| 2,342,029 | 2/1944 | Zubko | 73/15 |
| 2,779,189 | 1/1957 | Corneil | 73/15 X |
| 3,165,915 | 1/1965 | Parker et al. | 73/15 |
| 3,217,537 | 11/1965 | Hager, Jr. | 73/15 X |
| 3,279,239 | 10/1966 | Arends et al. | 73/15 |
| 3,290,924 | 12/1966 | Ebner et al. | 73/61.3 |
| 3,566,669 | 3/1971 | Lawrence et al. | 73/15 |
| 3,570,302 | 3/1971 | Sauer | 73/15 |
| 3,789,654 | 2/1974 | Jones | 73/15 |
| 3,795,133 | 3/1974 | Fergason et al. | 73/15 |

*Primary Examiner*—Herbert Goldstein
*Attorney, Agent, or Firm*—Arthur A. Smith, Jr.; Robert Shaw; Martin M. Santa

[57] ABSTRACT

A way to determine, nondestructively, the purity or composition of an unknown material sample such as, for example, a sample of gold or silver of unknown purity. The procedure involves subjecting one end of an elongate sample of known length and weight to a temperature elevated relative to that of the sample and comparing the time-varying temperature pattern at the other end thereof during finite lengths of time with that of a known or identically-sized standard subjected to equivalent or the same conditions for an interval of time of the same finite length. The temperature of said other end can be monitored during the time heat is applied and/or after it is withdrawn.

43 Claims, 3 Drawing Figures

METHOD OF AND APPARATUS FOR NONDESTRUCTIVELY DETERMINING THE COMPOSITION OF AN UNKNOWN MATERIAL SAMPLE

The present invention relates to the nondestructive testing of a material to determine its composition or purity by comparing the thermal properties of a sample of the material with the thermal properties of a standard of the same material, said standard having a desired composition or purity.

Although the invention herein described has use for the nondestructive qualitative determination of composition or purity of a variety of materials or substances, its use is discussed mostly with reference to gold and, to a lesser extent, silver. The rise in trading in recent years of gold, as a commodity, and the recent change in the laws in the United States has increased the need for an economical, fail-safe mechanism for determining nondestructively, the purity of gold. Since gold is often transferred by a person not particularly knowledgeable about gold to one of equal knowledge, it is important that some way be found to detect forgeries, a way that avoids the usual chemical determination, a way that is nondestructive, fast, and accurate. Since such transfer will often occur at banks and like institutions, any mechanism evolved should be sized to set on a counter, or desk; it must be suitable for operation by persons having little technical skill.

Accordingly, an object of the present invention is to provide for the nondestructive determination of purity of a material sample.

Another object is to provide a mechanism for such nondestructive determination, one that is relatively small, relatively inexpensive, fail-safe in determination, and one that can be operated by persons with only a small amount of technical training.

Still another object is to provide such mechanism for the nondestructive determination of the composition of gold bars of known length and known weight.

A further object is to provide such mechanism for nondestructive determination of the composition of silver bars.

A still further object is to provide the foregoing mechanism for the nondestructive determination of the composition or the purity of such gold bars or such silver bars in the form of samples and to give an indication or an alarm in the event that a particular sample fails to meet a standard.

Another object is to determine the moisture content and/or the degree of compaction of soils for use by construction engineers, for example.

Another object is to provide a characteristic temperature v. time curve or characteristic signature for various materials, substances, elements, etc.

These and still further objects are discussed in the description that follows and are particularly delineated in the appended claims.

The foregoing objects are achieved, broadly, in a method of determining nondestructively the composition of a sample of an unknown material by noting the thermal characteristics of the sample and matching or comparing said thermal characteristics with the thermal characteristics of a standard of the same general-type material and of known composition. The method includes controllably applying heat to the sample at a first region thereof to provide a time-varying temperature pattern in the sample, measuring the temperature of the same at a second region thereof a known distance from the first region, and comparing the time-varying temperature pattern for a finite length of time with a time-varying temperature pattern of the standard subjected to equivalent conditions for the same length of time.

The invention is hereinafter described with reference to the accompanying drawing in which.

In the description that now follows, the invention is first discussed with reference to a system for determining nondestructively the composition or the purity of an unknown sample in bar form and, to simplify the explanation, the sample first taken up is gold; but it will be kept in mind that most aspects of the system discussed with respect to gold apply also to other materials, as is noted elsewhere herein.

Figure 1:
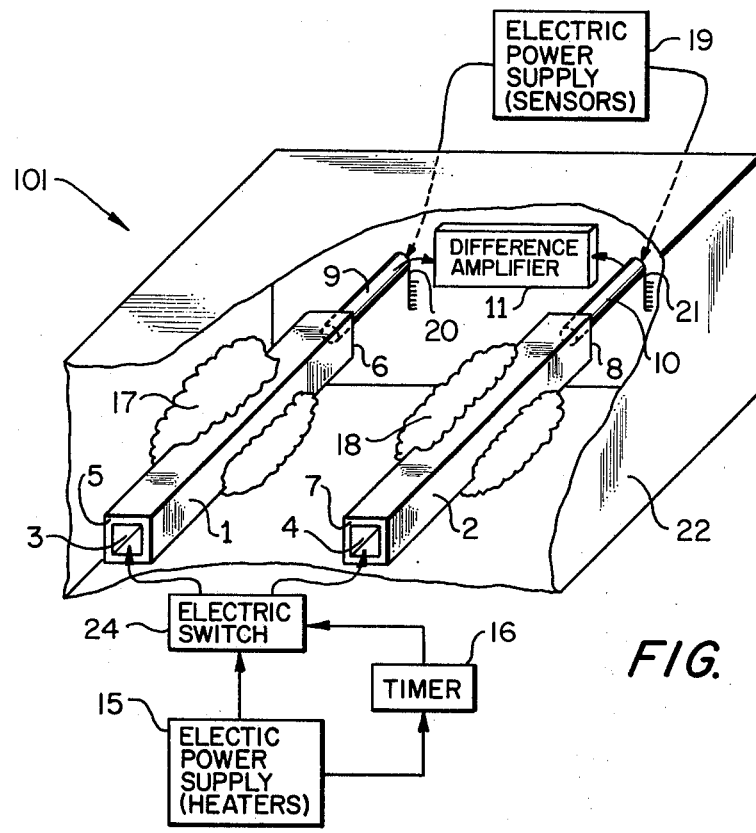
FIG. 1 is a diagrammatic representation, partly block diagram in form and with portions of the apparatus shown being partly cutaway, of a system adapted to effect nondestructive determination of the composition of a material sample.
Figure 2:
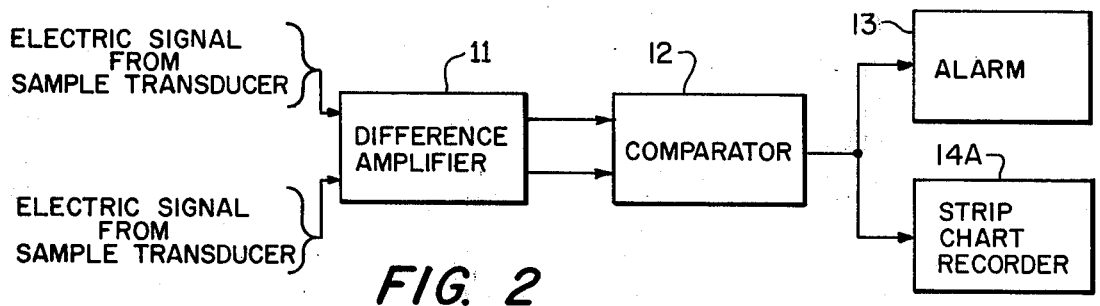
FIG. 2 shows in block diagram form a part of the system of FIG. 1, but slightly modified.

Turning now to FIG. 1, apparatus is shown at 101 for such nondestructive determination. In the system 101 of FIG. 1, a solid elongate sample or bar 1 of unknown precise composition or purity is compared with a solid standard 2 of known composition or purity, as now explained. An electric-resistance heater 3 applies heat to the sample 1 at a first region or end 5 thereof and, at the same time, a heater 4 applies heat to the standard 2 at a first region or end 7 thereof, thereby to provide time-varying temperature patterns in the sample and the standard. Simultaneously with or at a predetermined time after the heat is applied and for a predetermined time interval, the temperatures or the time-varying temperature patterns of the sample and of the standard are sensed or noted and compared. The sensing function is provided by transducers 9 and 10 operatively disposed to sense the time-varying temperatures at second regions 6 and 8 respectively of the sample and the standard, each of the transducers providing as output an electric signal that is a function of the time-varying temperature at the respective second region. The two electric signals are connected as inputs to a difference amplifer 11 which notes any difference between the two electric signals due to a temperature differential and amplifies the same. In FIG. 2, a comparator 12 is connected to receive an output from the difference amplifier 11 and is connected to an alarm 13 which is activated in those instances in which the purity of the sample 1 varies a predetermined amount from the standard 2, or to a strip chart recorder 14A. To complete the electric circuitry of FIG. 1 by which sample composition or purity is evaluated or analyzed, the heaters 3 and 4 are electrically energized through a switch 24 from an electric power source 15. The sequencing and timing of the events in the system 101 is provided by a timer or timer means 16.

In the apparatus 101 the heating elements 3 and 4 contact one end of the unknown sample and the associated bar of gold bullion, respectively, as above noted. The length and weight of each bar must be known. At the far end of each bar is an element (thermistor, thermocouple, or other transducer (powered if required)

by an electrical power source 19) to determine the temperature at said far end of each bar and, most importantly, to determine the relative changes in temperature at the far ends of the bars in some time pattern. The bars, heaters, and temperature sensing devices should be well insulated from the environment, but good thermal contact is essential between the bars and the heating elements and the bars and the temperature sensing devices. Axial forces are provided to maintain such contact by leaf or other light springs 20 and 21 that are insulated, thermally and electrically, from the transducers 9 and 10, respectively. Each bar, heating element, and temperature sensor should be well insulated from the other bar, heating element and temperature sensor. (In FIG. 1 the bars 1 and 2 are separated from one another, and thermal insulating material 17 and 18 is placed around the bars and between the bars. In actual apparatus made and tested in accordance with the present concepts, the housing labeled 22 within which the bars are placed has an insulating recess to receive each bar.) Each heater should be of a type that provides a controlled heat input as opposed to a constant temperature source; the heat thus applied is a controlled amount; and the resistances 3 and 4 for acceptable results must have low heat capacity so that most of the heat generated therein is transferred to the associated bars 1 and 2. Heaters found to be best when a concentrated amount of heat in a small area is required are strain gages of appropriate size, which strain gages can be compensated for changes in temperature.

If heat (e.g., a squarewave pulse of indefinite duration) is applied to one end of a bar at $x = l$, the general equation for the temperature at any distance $x$ (assuming the bar to be well insulated) is given by the expression:

$$T(x) = \frac{Ql}{k} \left\{ \frac{\alpha t}{l^2} + \frac{3x^2 - l^2}{6l^2} - \frac{2}{\pi^2} \sum_{n=1}^{\infty} \frac{(-1)^n}{n^2} \exp(-\alpha n^2 \pi^2 t/l^2) \cos \frac{n\pi}{l} x \right\} \quad (1)$$

where: Q is the suddenly applied constant heat flux per unit area (BTU/sec-ft²) at $x = l$,
$l$ is the length of the bar in feet,
$k$ is the thermal conductivity BTU/sec-ft-°F,
$\alpha$ is the thermal diffusivity in ft²/sec = $k/\alpha c$,
$\rho$ is the density in lbs/ft³,
$c$ is the specific heat BTU/lb-°F,
$t$ is time in seconds,
$x$ is the distance along the bar (note at $x = 0$ there is no flow of heat), and
$T(x)$ is temperature in °F.
(See Carslaw and Jaeger "Conduction of Heat in Solids," Oxford University Press 1950, page 104, paragraph 43, eq. (1).) If the temperature is measured at $x = 0$, the insulated end of the bar, equation (1) becomes:

$$T_{end} = \frac{Ql}{k} \left\{ \frac{\alpha t}{l^2} - \frac{1}{6} - \frac{2}{\pi^2} \sum_{n=1}^{\infty} \frac{(-1)^n}{n^2} \exp(\alpha n^2 \pi^2 t/l^2) \right\} \quad (1A)$$

If an attempt is made to counterfeit a bar of material, the weight w, in pounds, would be duplicated or can be easily measured. Thus, equation (1A) becomes:

$$T_{end} = \frac{q}{w} \left\{ \frac{t}{c} - \frac{l^2 \rho}{6k} - \frac{2l^2 \rho}{k\pi^2} \sum_{n=1}^{\infty} \frac{(-1)^n}{n^2} \exp(\alpha n^2 \pi^2 t/l^2) \right\} \quad (2)$$

where: $q$ is the suddenly applied constant heat flux in BTUs/sec. and all other terms are as defined above.

Gold has the third highest thermal conductivity and one of the lowest heat capacities. It develops that if the time period for testing is selected correctly, a pure gold bar will attain a higher end temperature than any other material.

After the heater is shut off, the temperature of the bar becomes:

$$qt/Wc$$

which provides a further check on authenticity.

Those metals (silver, copper) which have a higher thermal conductivity than gold have also much higher heat capacity, while those metals having lower heat capacity have very much lower thermal conductivities.

Thus, it is sufficient that at all times during the test interval, the temperature of the end of the bar suspected of forgery be as high or higher than that of the known gold (or a recording thereof) for certainty that the bar in question is as pure or purer than the standard. This is subject to several restrictions and possible errors which are taken up in the next paragraph.

The ratio $q_{sa}/W_{sa} = q_{st}/W_{st}$ (wherein $q_{sa}$ and $q_{st}$ are the heat inputs to the sample and a standard of respective weights $W_{sa}$ and $W_{st}$) must be kept within acceptable tolerance. The test is as good as the exactitude with which the lengths and weights are known. The thermal conductivity and density of $l$ are extremely high and the specific heat $c$ is low relative to most materials. A table of $c$ and the ratio $\rho/k$ is presented in Table I below for gold and for most materials likely to be used as an adulterant. Ideally, the ratio $(q/W)$ should be as high as possible for maximum sensitivity. Lower values of this ratio can be compensated for by more sensitive instrumentation methods or amplification of temperature differences. If the bar is too short temperature differences will be difficult to detect with accuracy and low $c$ values could dominate. The factor $l^2$ in equations (1), (1A) and (2) is very important for the sensitivity of the test.

TABLE I

| | c<br>BTU<br>lb - °F | ρ/k<br>lb - sec - °F<br>BTU - ft² |
|---|---|---|
| Gold | .030 | 23.6 × 10³ |
| Silver | .056 | 9.5 × 10³ |
| Copper | .092 | 8.7 × 10³ |
| Uranium | .030 | 267.3 × 10³ |
| Lead | .030 | 124.7 × 10³ |
| Platinum | .031 | 116.2 × 10³ |
| Tungsten | .031 | 43.3 × 10³ |

Before turning to a discussion of the present invention with reference to silver and other materials, a few further general comments that apply mostly to gold are in order. Typically, the same amount of heat is applied to one end of two identically-sized bars. For some time interval, the temperature of the two at the other or far end of each is taken and the two are compared. Most adulterated samples tested in the course of the work leading to and arising from this invention will be cooler at that other or far end than will be the pure gold standard, but that is not always the case. Hence, the temperatures at the far end of each bar is taken over some time interval after heat is applied, depending on the length of the bar and other factors. For example, bars of length 0.378 ft, weight 2.2 pounds, of uniform cross dimensions are sampled for eighty seconds after the heat is applied. In this circumstance an adulterated sample will always be cooler at the far end or second region than the standard at some point during that time interval. Also, the heaters 3 and 4 can be de-energized and the time-varying, but declining, temperature patterns can be noted and compared.

Figure 3:
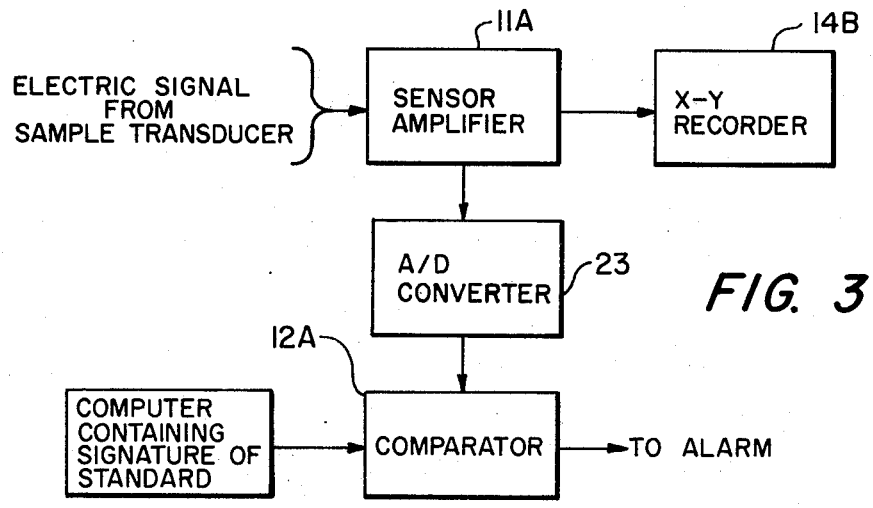
FIG. 3 shows in block diagram form another modified version of a part of the system of FIG. 1.

It is not necessary that the standard actually be present at the time the sample is tested. Thus, in FIG. 3 the time-varying pattern of a sample, converted to an electric signal as before, is fed to a sensor amplifier 11A and thence to an analog-to-digital converter 23, the output of the converter being connected as one input to a comparator 12A (see Baker Letters Pat. No. 3,705,391), the other input to which is from a computer which has stored the signature of an equivalent standard (see Senturia et al Letters Pat. No. 3,747,755). The output of the comparator 12A can connect to an alarm. Also, the sensor output can be connected as input to an X-Y recorder 14B.

It is assumed now that the bars 1 and 2 are silver. If a constant temperature source is applied to one end of a bar, the equation for the temperature at the far end is given by (assuming the bar is well insulated):

$$T_{end} = 2T_0 \sum_{n=0}^{\infty} (-1)^n \left\{ 1 - (\text{erf}) \left[ \frac{(2n+1)}{2\sqrt{\frac{\alpha T}{l^2}}} \right] \right\} \quad (3)$$

where:

$T_{end}$ is the temperature in °F above ambient at the end, of the bar opposite the constant temperature source, $T_0$ is the suddenly applied constant temperature in °F above ambient, erf is the standard definition of error function and is well tabulated in many references, $\alpha$ is the thermal diffusivity of the bar in ft²/sec $= k/\rho c$, $t$ is the time in seconds, and $l$ is the length of the bar in ft.

Silver has the highest thermal diffusivity of any known metallic material. Therefore, as a function of time, the silver bar will attain a higher far end temperature than any other material. Thus, it is sufficient that at any time during the test, the temperature of the known silver bar (or a recording thereof) be lower than that of the bar suspected of forgery, for certainty that the bar in question is as pure or purer than the standard. Again, this is subject to restrictions and several possible errors, as now discussed.

$T_0$ must be identical for the sample and the standard. The test is as good as the exactitude with which the lengths of the bars are known. The thermal diffusivity of silver is very high compared to most materials. A table of $\alpha$ (Table II hereinafter) is presented for silver and for most materials likely to be used as adulterants of silver. The length of the bar is very important for the sensitivity of the test. Ideally, this should be as long as possible for maximum sensitivity. Lower length values can be compensated for by more sensitive instrumentation for amplification of temperature differences.

TABLE II

| | $\alpha$ ft²/sec |
|---|---|
| Silver | $1.88 \times 10^{-3}$ |
| Copper | $1.26 \times 10^{-3}$ |
| Zinc | $0.45 \times 10^{-3}$ |
| Molybdemium | $0.58 \times 10^{-3}$ |
| Palladium | $0.26 \times 10^{-3}$ |

Other materials can be similarly tested for composition. Thus, by way of illustration, soil samples can be checked for degree of compaction or moisture content. This can be accomplished using a recorder 14A or 14B for example, which can contain a trace or pattern of an acceptable or a known standard against which the time-varying temperature pattern of a sample can be visually compared. In testing soil samples by the present system, what is really done is to determine the ratio of fluid-to-solid (i.e., gas or water content to solid) in the sample.

The apparatus herein disclosed provides fast, foolproof and economical determination of composition, purity and thermal properties of samples in a system which avoids the high skill needed for such determination by observing surface properties, the multiple tests of chemical analysis, and the destruction of the sample ingot in the case of gold and silver. It makes possible such analysis by unskilled persons in a go-no-go type mode of operation. In the case of many materials, it makes possible testing and checking of samples for which no known process is presently available. The accuracy of results is related to the length of the sample as well as the quality of the electronics employed, but purity of gold samples can be sensed and the quality thereof noted to 99.5% pure and better.

Further modifications of the invention herein disclosed will occur to persons skilled in the art and all such modifications are deemed to be within the spirit and scope of the invention as defined by the appended claims.

What is claimed is:

1. Apparatus for determining nondestructively the composition of an unknown sample that comprises, in combination: means for applying heat at a rate $q_{sa}$ at one end of an elongate sample of weight $W_{sa}$; means for simultaneously applying heat at a rate $q_{st}$ at one end of a standard of weight $W_{st}$ and having the same length as the length of the sample such that $q_{sa}/W_{sa} = q_{st}/W_{st}$; first transducer means positioned to sense the temperature at the other end of the sample and to provide a first electric signal; second transducer means positioned to sense the temperature at the other end of the standard and to provide a second electric signal; and means connected to receive and analyze the first electric signal and the second electric signal over time to determine the relative magnitudes, either qualitatively or quantitatively, of the temperatures at the ends of the sample and of the standard.

2. Apparatus as claimed in claim 1 in which the means for applying heat to the sample is a first source operable to effect transfer of a controlled amount of heat to the sample and the means for applying heat to the standard is a second source operable to effect transfer of a controlled amount of heat to the standard.

3. Apparatus as claimed in claim 1 in which the sample and the standard are thermally insulated from each other and from the environment.

4. Apparatus for determining nondestructively the composition of an unknown elongate sample that comprises, in combination: means for applying heat to the sample at a first region of the sample; means for sensing the resulting time-varying temperature of the sample at a second region of the sample remote from the first region thereof; a known standard of the same length as the sample; means for applying heat to the standard at a first region of the standard; means for sensing the resulting time-varying temperature of the standard at a second region remote from the first region thereof; and means for simultaneously comparing the time-varying temperature pattern for a predetermined finite length of time at said second region of the sample with a time-varying temperature pattern of the known standard of the same length subjected to equivalent conditions for the same finite length of time.

5. Apparatus as claimed in claim 4 in which the material sample is a gold bar of alleged high purity, in which the standard is a pure gold bar of the same length and weight as the sample, in which the means for applying heat is a first electric resistance operatively disposed to deliver heat to the sample and having low heat capacity so that most of the heat generated in the electric resistance is transferred to the alleged gold sample and a second electric resistance substantially identical to the first electric resistance and operatively disposed to deliver heat to the standard, the heat being delivered at one end of each bar and the temperature being sensed at the other end of each bar.

6. Apparatus as claimed in claim 5 in which the means for sensing comprises a transducer operationally positioned at said other end of each bar to sense the temperature there and to convert each to an electric signal and in which the means for comparing comprises electric circuitry connected to receive the electric signal from each transducer and to compare one with the other.

7. Apparatus as claimed in claim 5 in which the means for sensing the resulting time-varying temperature at the second region of the sample comprises a first transducer operatively disposed to sense the temperature at the second region of the sample as input and to provide as output a first electric signal that varies as a function of the input temperature to the first transducer and in which the means for sensing the resulting time-varying temperature at the second region of the standard comprises a second transducer operatively disposed to sense the temperature at the second region of the standard as input and to provide as output a second electric signal that varies as a function of the input temperature to the second transducer.

8. Apparatus as claimed in claim 7 that further includes means for comparing the first electric signal with the second electric signal.

9. Apparatus as claimed in claim 8 that further includes an alarm connected to receive a message from the means for comparing and to be selectively activated thereby.

10. Apparatus as claimed in claim 9 in which said means for comparing is operable to compare the signals at each instant of time during said finite length of time and acts to activate the alarm if at any point in time during the said finite length of time the temperature of the sample at said second region of the sample is lower than the temperature of the standard at said second region of the standard by some predetermined amount.

11. Apparatus as claimed in claim 7 in which the sample and the standard are thermally insulated from each other and from the environment.

12. Apparatus as claimed in claim 4 in which the means for applying heat to the sample is a first constant temperature source and the means for applying heat to the standard is a second constant temperature source.

13. Apparatus as claimed in claim 12 wherein the sample is a silver bar of alleged high purity, in which the standard is a pure silver bar of the same length as the sample, the comparison being made to detect forgeries.

14. Apparatus as claimed in claim 13 in which the means for sensing the resulting time-varying temperature at the second region of the sample comprises a first transducer operatively disposed to sense the temperature at the second region of the sample as input and to provide as output a first electric signal that varies as a function of the input temperature to the first transducer and in which the means for sensing the resulting time-varying temperature at the second region of the standard comprises a second transducer operatively disposed to sense the temperature at the second region of the standard as input and to provide as output a second electric signal that varies as a function of the input temperature to the second transducer.

15. Apparatus as claimed in claim 14 in which the means for comparing comprises means for comparing the first electric signal with the second electric signal.

16. Apparatus as claimed in claim 15 that further includes an alarm connected to receive a message from the means for comparing and to be selectively activated thereby.

17. Apparatus as claimed in claim 16 in which said means for comparing is operable to compare the signals at each instant of time during said finite length of time and acts to activate the alarm if at any point in time during the said finite length of time the temperature of the sample at said second region of the sample is lower than the temperature of the standard at said second region of the standard by some predetermined amount.

18. Apparatus as claimed in claim 17 in which the sample and the standard are thermally insulated from each other and from the environment.

19. Apparatus as claimed in claim 4 in which the means for sensing the resulting time-varying temperature at the second region of the sample comprises a first transducer operatively disposed to sense the temperature at the second region of the sample as input and to provide as output a first electric signal that varies as a function of the input temperature to the first transducer and in which the means for sensing the resulting time-varying temperature at the second region of the standard comprises a second transducer operatively disposed to sense the temperature at the second region of the standard as input and to provide as output a second electric signal that varies as a function of the input temperature to the second transducer.

20. Apparatus as claimed in claim 19 that further includes means for comparing the first electric signal with the second electric signal.

21. Apparatus as claimed in claim 20 that further includes an alarm connected to receive a message from the means for comparing and to be selectively activated thereby.

22. Apparatus as claimed in claim 21 in which said means for comparing is operable to compare the signals at each instant of time during said finite length of time and acts to activate the alarm if at any point in time during the said finite length of time the temperature of the sample at said second region of the sample is lower than the temperature of the standard at said second region of the standard by some predetermined amount.

23. Apparatus as claimed in claim 22 wherein both the sample and the standard are gold and wherein the means for applying heat to each is a controlled source of heat.

24. Apparatus as claimed in claim 22 in which the sample and the standard are equal in length and are respectively of weight $W_{sa}$ and $W_{st}$, in which the respective heat inputs are $q_{sa}$ and $q_{st}$, and in which the ratio of heat input-to-weight is $q_{sa}/W_{sa} = q_{st}/W_{st}$.

25. Apparatus as claimed in claim 22 wherein $W_{sa} \gg W_{st}$.

26. Apparatus as claimed in claim 21 having timing means that serves to sequence the means for applying heat to both the sample and the standard as well as the sensing functions of the transducers.

27. Apparatus as claimed in claim 26 in which the sample is a bar of weight $W_{sa}$ and the standard is a bar the same length as the sample and of weight $W_{st}$, in which the means for applying heat to the sample supplies the heat at a rate $q_{sa}$ and the means for supplying heat to the standard supplies the heat at a rate of $q_{st}$, the ratio of heat-to-weight being $q_{sa}/W_{sa} = q_{st}/W_{st}$.

28. Apparatus as claimed in claim 4 in which the means for sensing the resulting time-varying temperature at the second region of the sample comprises a transducer operatively disposed to sense the temperature at the second region of the sample as input and to provide as output an electric signal that varies as a function of the input temperature to the transducer and in which the means for comparing comprises computer means connected to receive the electric signal and to compare it with a time-varying temperature pattern of a known standard.

29. Apparatus as claimed in claim 28 in which the computer means comprises: an analog-to-digital converter connected to receive the electric signal and to convert it to a digital signal, a computer having in memory a digital signal representative of the time-varying temperature pattern of the known standard, and a comparator connected to receive the digital signal from the analog-to-digital converter and the digital signal from the computer, to compare the same and to provide an output indicative of the relative magnitudes of the two at each point in time for said finite length of time.

30. Apparatus as claimed in claim 29 that further includes an alarm connected to receive the output of the comparator and provide an indication in the event that said relative magnitudes vary more than some predetermined small amount from one another at any point in time during the said finite length of time.

31. Apparatus as claimed in claim 4 in which the material sample is a soil sample and in which the apparatus is operable to detect relative magnitudes of solids and fluids in the sample.

32. Apparatus as claimed in claim 4 wherein the means for comparing comprises means for making a visual record of the timevarying temperature pattern of the sample so that the sample pattern can be visually compared with a similar-type visual record of the standard.

33. A method of determining nondestructively the composition of an unknown material sample, that comprises: applying heat at a first region of an elongate sample of said material to provide a time-varying temperature patern in the sample; controlling the rate of heat input to the sample; measuring the temperature as a function of time at a second region of the sample a known distance from the first region; and simultaneously comparing the timevarying temperature pattern for a predetermined finite length of time at said second region of the sample with a time-varying temperature pattern of a known standard subjected to equivalent conditions for the same length of time, the sample and the standard being of the same length and being simultaneously subjected to heat input at a constant rate at a first region of each, the temperature of each being sensed at a second region displaced from the first region at a known distance, and the temperature of the sample at the second region thereof being compared to the temperature of the standard at the second region thereof continuously and for a finite length of time.

34. A method as claimed in claim 33 that further includes discontinuing the application of heat to the sample and comparing the resulting time-varying temperature pattern for a predetermined finite length of time after the discontinuation of the heat with the time-varying temperature pattern of a known standard subject to equivalent conditions for the same length of time.

35. A method as claimed in claim 33 in which the sample is compared to that of a standard of the same weight.

36. A method as claimed in claim 33 wherein the sample has applied to it heat at some temperature level and the standard is subject to heat at the same temperature level.

37. A method as claimed in claim 36 wherein the sample and the standard are simultaneously subjected to equal temperature at a first region of each, wherein the temperature of each is sensed at a second region displaced from the first region a known and equal distance, for a finite length of time, and wherein the temperature at the second region of the sample is compared to the temperature of the standard during said finite length of time.

38. A method as claimed in claim 37 in which the sample and the standard are each an elongate silver bar, in which the first region of the sample and the standard is one end of the respective bar and in which the second region of the sample and the standard is the other end of the respective bar.

39. A method as claimed in claim 33 wherein the sample is a soil sample and wherein the temperature at said second region is sensed to determine the ratio of solid-to-fluid in the sample by comparing the time-varying temperature with respect to the sample to the time-varying temperature pattern with respect to a standard of a known ratio of solid-to-fluid.

40. A method as claimed in claim 39 wherein the fluid is water and whereby determination of the ratio establishes the water content in the sample.

41. A method as claimed in claim 33 wherein the sample and the standard are each an elongate bar; in which the sample is allegedly gold of high purity; in which the standard is a pure gold bar; in which the first region of the sample and the standard is one end of the respective bar and in which the second region of the sample and the standard is the other end of the respective bar.

42. A method as claimed in claim 41 wherein the sample and the standard are of the same weight and are each subjected to an identical heat input for an identical period of time.

43. A method of determining nondestructively whether an unknown elongate sample bar is at least as pure as an elongate standard bar of gold of known high purity and of the same length as the length of the sample or varies in purity by an acceptable amount, that comprises: applying heat at a first region of the sample bar to provide a time-varying temperature pattern in the sample; controlling the rate of heat input to the sample; measuring the temperature as a function of time at a second region of the sample a known distance from the first region; and comparing the time-varying temperature pattern for a predetermined finite length of time at said second region of the sample with a time-varying temperature pattern at a second region of a known standard subjected to the same heat input at a first region thereof for the same length of time, the second region of the standard being the same known distance from the first region thereof, to determine whether relative temperature changes of the sample are at all times at least as great at the second region thereof as relative changes in temperature of the standard at said second region thereof or said changes in temperature are lower than the changes in temperature of the standard at said second region of the standard by some acceptable predetermined small amount.

* * * * *

UNITED STATES PATENT OFFICE
CERTIFICATE OF CORRECTION

Patent No. 3,981,175              Dated September 21, 1976

Inventor(s) Ogden H. Hammond III et al.

It is certified that error appears in the above-identified patent and that said Letters Patent are hereby corrected as shown below:

Column 3, line 52, after "in," change expression to read:
-- $ft^2/sec = k/pc$, --

Column 4, change expression "(2)" to read $$T_{end} = \frac{q}{w} \left\{ \frac{t}{c} - \frac{\ell^2 \rho}{6k} - \frac{2\ell^2 \rho}{k\pi^2} \sum_{n=1}^{\infty} \frac{(-1)^n}{n^2} \exp(-\alpha n^2 \pi^2 t/\ell^2) \right\}$$

Signed and Sealed this

Seventeenth Day of May 1977

[SEAL]

Attest:

RUTH C. MASON  
*Attesting Officer*

C. MARSHALL DANN  
*Commissioner of Patents and Trademarks*